(12) United States Patent
Chase

(10) Patent No.: US 12,605,160 B2
(45) Date of Patent: Apr. 21, 2026

(54) BLEEDING CONTROL DEVICE

(71) Applicant: William Chase, Avon, CT (US)

(72) Inventor: William Chase, Avon, CT (US)

( * ) Notice: Subject to any disclaimer, the term of this patent is extended or adjusted under 35 U.S.C. 154(b) by 0 days.

(21) Appl. No.: 18/413,437

(22) Filed: Jan. 16, 2024

(65) Prior Publication Data

US 2024/0148386 A1     May 9, 2024

Related U.S. Application Data

(60) Division of application No. 18/170,112, filed on Feb. 16, 2023, which is a continuation-in-part of application No. 16/867,798, filed on May 6, 2020, now Pat. No. 11,583,285, which is a division of application No. 16/733,655, filed on Jan. 3, 2020, now Pat. No. 11,259,813.

(60) Provisional application No. 62/815,632, filed on Mar. 8, 2019.

(51) Int. Cl.
*A61B 17/12* (2006.01)
*A61B 17/00* (2006.01)

(52) U.S. Cl.
CPC .................. *A61B 17/12136* (2013.01); *A61B 2017/00548* (2013.01); *A61B 2017/12004* (2013.01); *A61B 17/1204* (2013.01)

(58) Field of Classification Search
CPC .............. A61B 17/135; A61B 17/1325; A61B 17/1355; A61B 17/12136; A61B 17/12022; A61B 17/12027; A61B 17/1204; A61B 17/12031; A61B 2017/12004; A61B 2017/00548; A61B 2017/1205; A61B 2017/0065
See application file for complete search history.

(56) References Cited

U.S. PATENT DOCUMENTS

| | | | |
|---|---|---|---|
| 4,479,497 A | 10/1984 | Fogarty et al. | |
| 5,307,811 A | * 5/1994 | Sigwart | A61B 17/132 |
| | | | 600/490 |
| 5,342,305 A | 8/1994 | Shonk | |

(Continued)

FOREIGN PATENT DOCUMENTS

| | | | |
|---|---|---|---|
| CN | 210494163 U | 5/2020 | |
| WO | WO-9846144 A1 | * 10/1998 | A61B 17/135 |
| WO | 2021163512 A1 | 8/2021 | |

OTHER PUBLICATIONS

Office Action of corresponding Canadian Application No. 3,210,356 dated Dec. 20, 2024.

*Primary Examiner* — Tuan V Nguyen
(74) *Attorney, Agent, or Firm* — McCormick, Paulding & Huber PLLC

(57) ABSTRACT

A bleeding control device for mitigating bleeding includes a housing, inflation means, an inflatable balloon and a gas supply line. The bleeding control device may be used to deliver variable contents to a wound at the site of injury to control the bleeding of a victim as temporary solution for mitigating the bleeding until more advanced medical care can be provided. A bleeding control device includes a canister housing, a compressed gas canister arranged within the canister housing, a tube connected to the canister housing, an inflatable balloon disposed on the tube, the inflatable balloon being fluidly connected to the compressed gas canister, and a control element configured to activate the compressed gas canister to inflate the inflatable balloon.

24 Claims, 12 Drawing Sheets

(56)  References Cited

U.S. PATENT DOCUMENTS

| | | | |
|---|---|---|---|
| 6,306,154 B1 | 10/2001 | Hudson et al. | |
| 7,591,830 B2 * | 9/2009 | Rutter | A61M 25/104 |
| | | | 128/207.15 |
| 11,122,970 B2 | 9/2021 | Piskun et al. | |
| 2002/0161388 A1 * | 10/2002 | Samuels | A61M 25/10 |
| | | | 428/36.9 |
| 2005/0137622 A1 | 6/2005 | Griffin | |
| 2007/0031283 A1 * | 2/2007 | Davis | A61B 5/150786 |
| | | | 422/400 |
| 2008/0071202 A1 * | 3/2008 | Nardi | A61H 11/00 |
| | | | 601/97 |
| 2010/0121270 A1 | 5/2010 | Gunday et al. | |
| 2010/0168784 A1 | 7/2010 | Pustilnik | |
| 2011/0152683 A1 | 6/2011 | Gerrans et al. | |
| 2011/0251636 A1 * | 10/2011 | McEwen | A61B 8/06 |
| | | | 606/202 |
| 2012/0197193 A1 | 8/2012 | Krolik et al. | |
| 2012/0259217 A1 | 10/2012 | Gerrans et al. | |
| 2013/0226219 A1 * | 8/2013 | Brister | A61F 5/0043 |
| | | | 606/192 |
| 2014/0025103 A1 | 1/2014 | Hundertmark et al. | |
| 2014/0276541 A1 * | 9/2014 | Ahluwalia | A61M 25/10184 |
| | | | 604/97.02 |
| 2015/0045826 A1 | 2/2015 | Drasler et al. | |
| 2018/0153557 A1 * | 6/2018 | Dimino | A61B 17/1327 |
| 2020/0281599 A1 | 9/2020 | Chase | |
| 2021/0145450 A1 | 5/2021 | Gruentzig | |

* cited by examiner

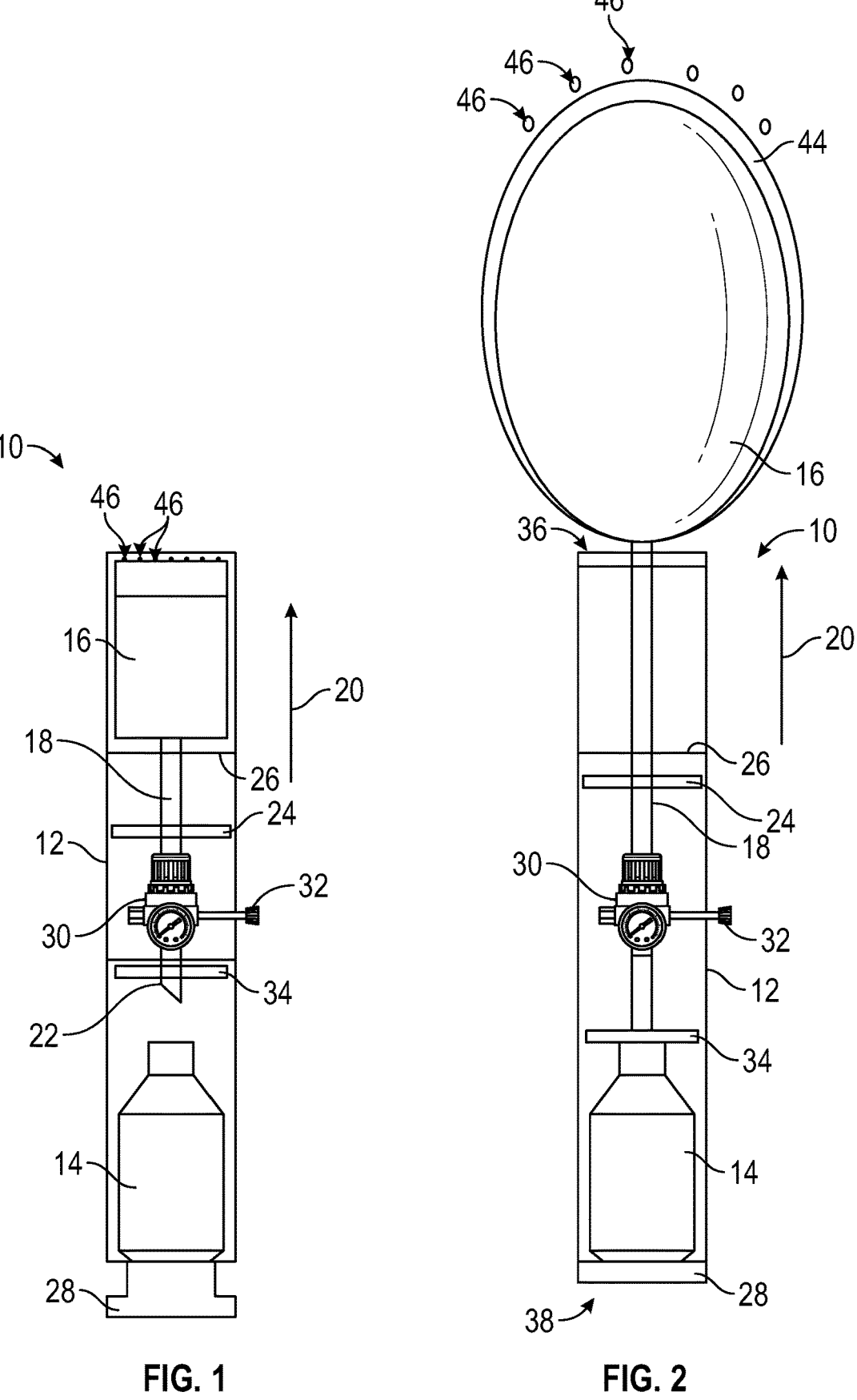
FIG. 1          FIG. 2

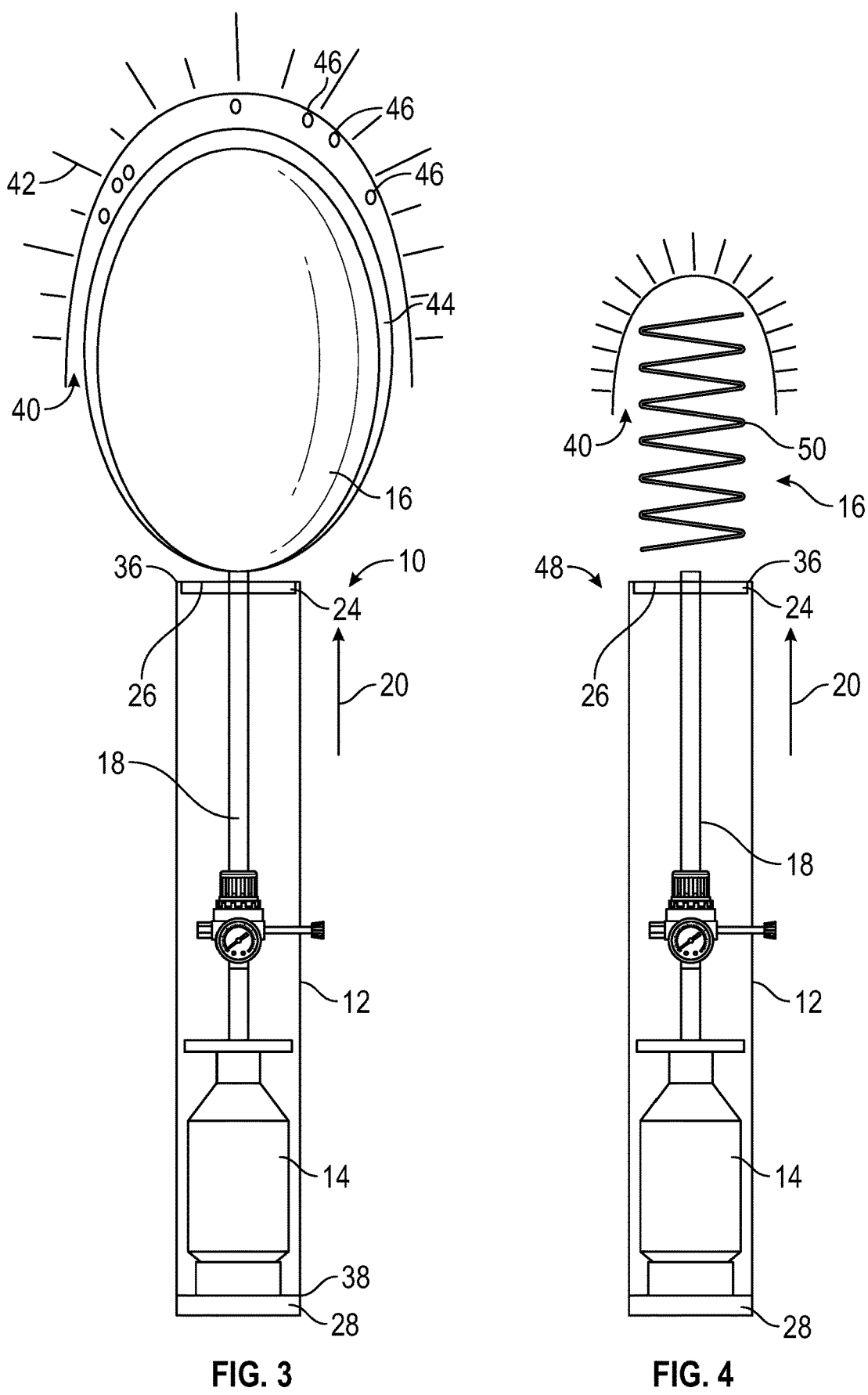
FIG. 3          FIG. 4

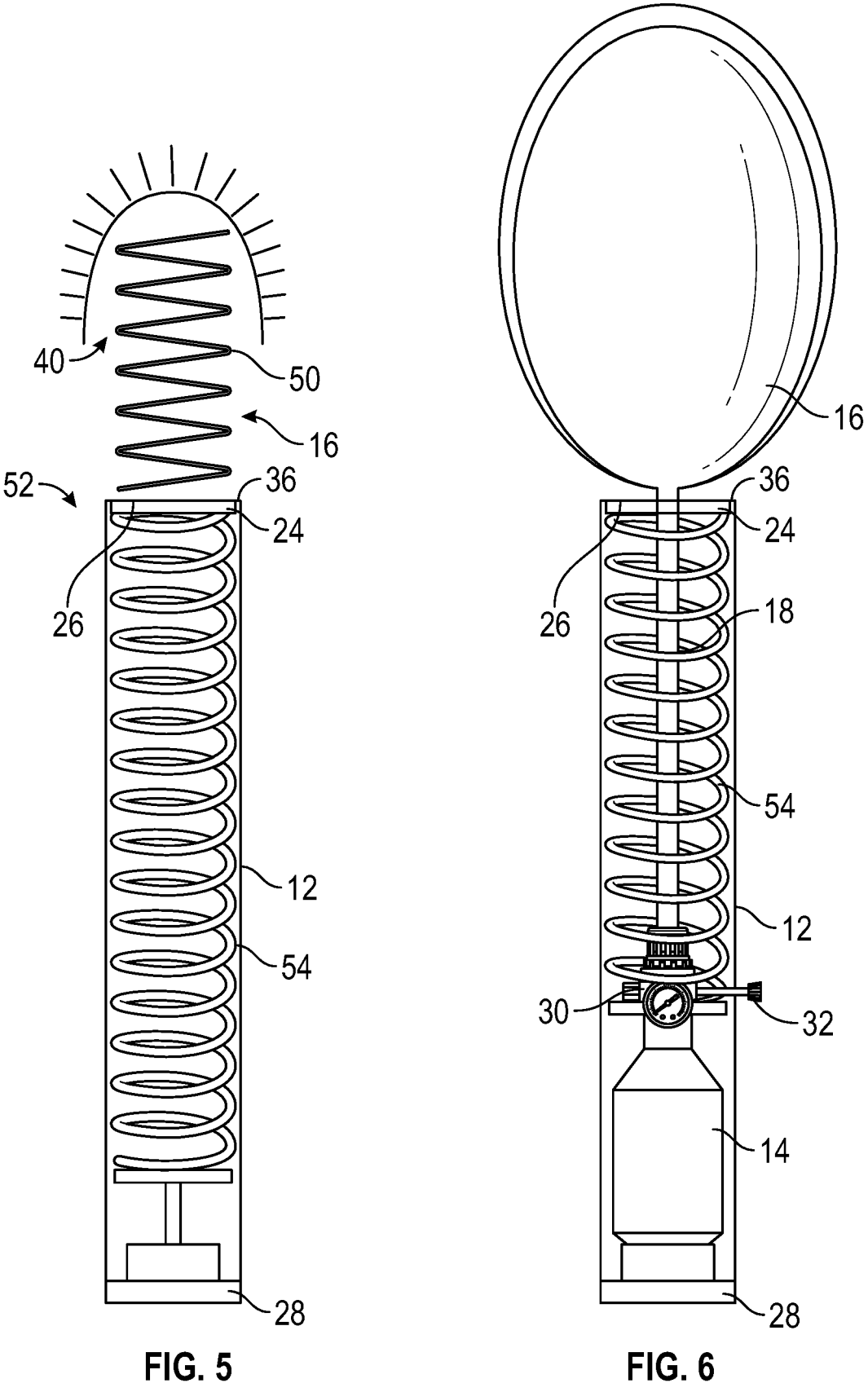
FIG. 5          FIG. 6

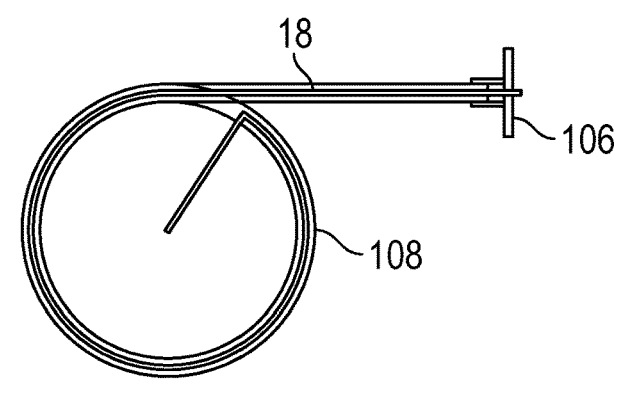
FIG. 16C
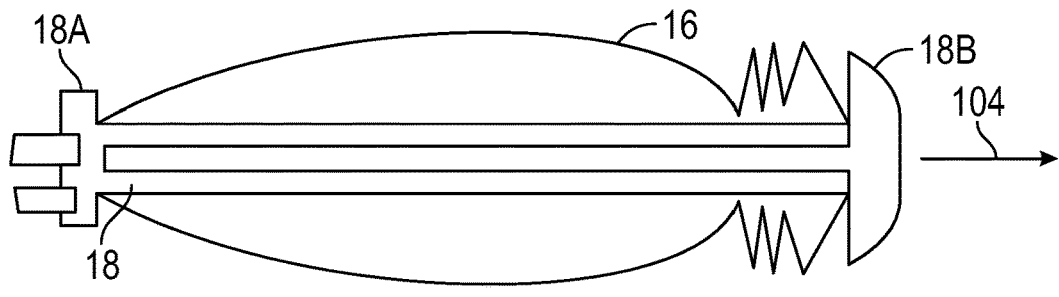
FIG. 17
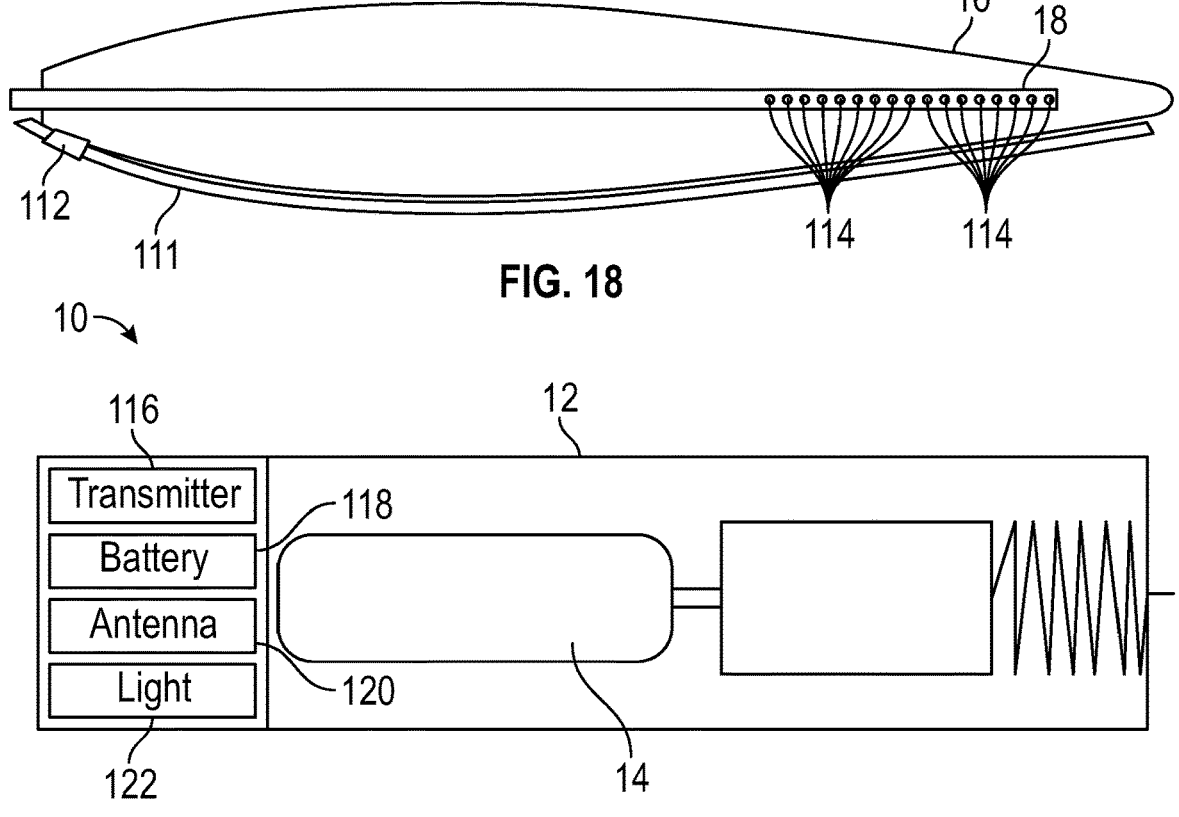
FIG. 18
FIG. 19

10

14      30      82

Regulator

134      Luer Lock Connection

10

116      82      16

Transmitter      118      14      30      18

Battery      Air Cylinder      Regulator

Antenna      120

Light 122      136

14      30      82      16      138

Air Cylinder      Regulator

18

BLEEDING CONTROL DEVICE

CROSS-REFERENCE TO RELATED APPLICATIONS

This application is a divisional of U.S. patent application Ser. No. 18/170,112, filed Feb. 16, 2023, which is a continuation-in-part of U.S. patent application Ser. No. 16/867, 798, filed on May 6, 2020, which is a divisional of U.S. patent application Ser. No. 16/733,655, filed on Jan. 3, 2020, which claims the benefit of U.S. Provisional Patent Application No. 62/815,632, filed on Mar. 8, 2019, each of which is incorporated herein by reference in its entirety.

TECHNICAL FIELD

The present disclosure generally relates to bleeding control at or near the site of an injury at the time when traumatic injury occurs, and more particularly, to an apparatus and method for quickly and efficiently covering and blocking a wound to control bleeding without needing advanced knowledge of first aid procedures.

BACKGROUND

Current bleeding control techniques for rapid blood loss include applying a tourniquet above a bleeding injury and/or packing a wound with gauze and applying pressure to the wound to reduce bleeding. In either case, if pressure is reduced, even for a short duration, any clots that have formed to slow bleeding may become ruptured and dislodged, causing bleeding to resume at a flow level comparable to the bleeding prior to treatment being applied. Additionally, typical wound packing must be done at a given density, generally immediately following the injury, otherwise the blood flow may not be slowed to an acceptable level. Moreover, some first aid training must have been acquired for effective use of such prior art techniques, or treatment may not extend the very short duration between untreated bleeding wounds and death. Accordingly, there is a need for a device that can be deployed with minimal effort to assist in such situations and assist in controlling and mitigating bleeding, that is, moreover, portable and easy enough to use in trauma situations by a layperson.

SUMMARY

In embodiments according to the present disclosure a bleeding control device includes an outer storage container housing, a compressed gas canister arranged within the outer storage container housing, wound blocking content arranged within the outer storage container housing, and an input element configured to activate the compressed gas canister to deploy the wound blocking content from the outer storage container housing.

In embodiments according to the present disclosure a bleeding control device includes an outer storage container housing, a compressed spring arranged within the outer storage container housing, wound blocking content arranged within the outer storage container housing, and an input element configured to activate the compressed spring to deploy the wound blocking content from the outer storage container housing.

In embodiments according to the present disclosure a bleeding control device includes a canister housing, a compressed gas canister arranged within the canister housing, a tube connected to the canister housing, an inflatable balloon disposed on the tube, the inflatable balloon being fluidly connected to the compressed gas canister, and an input element configured to activate the compressed gas canister to inflate the inflatable balloon.

Objects, features and advantages of the present invention will become apparent in light of the description of embodiments and features thereof, as enhanced by the accompanying figures.

BRIEF DESCRIPTION OF THE DRAWINGS

FIG. 1 is an illustration of a bleeding control device in a non-deployed state in accordance with the present disclosure;

FIG. 2 is an illustration of the bleeding control device of FIG. 1 in a deployed state in accordance with the present disclosure;

FIG. 3 is an illustration of a variant embodiment of the bleeding control device of FIG. 1 in a deployed state in a wound of a patient in accordance with the present disclosure;

FIG. 4 is an illustration of a bleeding control device in a deployed state in accordance with the present disclosure;

FIG. 5 is an illustration of a bleeding control device in a deployed state in accordance with the present disclosure;

FIG. 6 is an illustration of a bleeding control device in a deployed state in accordance with the present disclosure;

FIG. 16C shows a bleeding control device gas supply line and case in accordance with the present disclosure;

FIG. 17 shows a bleeding control device balloon and gas supply line in accordance with the present disclosure;

FIG. 18 shows a bleeding control device balloon and gas supply line in accordance with the present disclosure;

FIG. 19 shows a bleeding control device in accordance with the present disclosure;

DETAILED DESCRIPTION

Figure 7A:
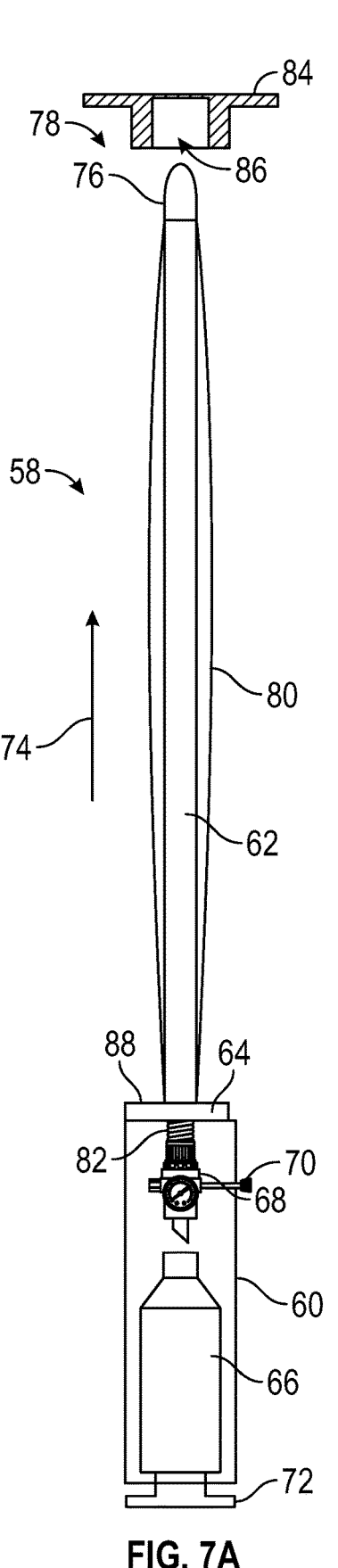
FIG. 7A is an illustration of a bleeding control device in a non-deployed state in accordance with the present disclosure.

Referring to FIG. 1, a schematic illustration of a bleeding control device 10 is shown in a non-deployed state in accordance with the present disclosure. The device 10 comprises an outer storage container housing 12, a compressed gas canister 14, wound blocking content(s) 16 and a gas supply line 18 connected to the wound blocking contents 16. The outer storage container housing 12 has a tubular-shaped body that extends in a longitudinal direction 20 from a proximate end 38 to a distal end 36. The compressed gas canister 14 is disposed within the outer storage container housing 12 proximate the proximate end 38 and the wound blocking contents 16 is disposed within the outer storage container housing 12 proximate the distal end 36. The gas supply line 18 extends in the longitudinal direction 20 within the outer storage container housing 12 from the wound blocking contents 16 to a piercing end 22 proximate to the compressed gas canister 14. A piston 24 is arranged within the outer storage container housing 12 between the compressed gas canister 14 and the wound blocking contents 16, with the gas supply line 18 extending through the piston 24. The piston 24 is movable along the gas supply line 18 in the longitudinal direction 20 and is configured to drive the wound blocking contents 16 from the device 10. The device 10 further comprises an activator 28 configured to activate the compressed gas canister 14 and/or actuate the compressed the gas canister 14. The activator 28 may be, for example, a mechanism that pierces the gas canister 14 to release the compressed gas, a controllable valve that is opened through a user input such as a button, switch or the like to release the compressed gas, or any other known mechanism for controlling the flow of gas from a reservoir. In the embodiment shown in FIG. 1, the wound blocking contents 16 is an inflatable balloon that is configured to be inflated by compressed gas from the compressed gas canister 14 when the compressed gas canister 14 is activated by the activator 28. The bleeding control device 10 may be configured to output gas flow from the compressed gas canister 14 at a fixed preset pressure level to inflate the inflatable balloon to the fixed pressure level.

The bleeding control device 10 may optionally comprise a regulator 30 configured to control the output gas flow from the compressed gas canister 14 when activated. The flow through the regulator 30 may be variably controlled and/or set to a desired pressure output through an adjustable control 32. When the optional regulator 30 is included, the inflatable balloon 16 may be inflated to a desired or predetermined pressure (and maintain that pressure) as is discussed in greater detail below. In some embodiments, the regulator 30 may be connected directly or indirectly with the compressed gas canister 14, and an input element, such as the activator 28 or the adjustable control 32, is configured to cause the regulator 30 to activate the compressed gas canister 14 by causing the regulator 30 to open the compressed gas canister 14 without the need to pierce the compressed gas canister 14. For example, the regulator 30 may be in the form of a valve that determines an opening degree of the compressed gas canister 14.

As seen in FIG. 1, the bleeding control device 10 may also comprise an optional stop 34 that prevents the piston 24 and/or wound blocking contents 16 from being introduced too far into the bleeding control device 10.

Referring to FIG. 2, a schematic illustration of the bleeding control device 10 of FIG. 1 is shown in a deployed state. To change the bleeding control device 10 from the non-deployed state shown in FIG. 1 to the deployed state of FIG. 2, the activator 28 is actuated by a user. In this embodiment, the activator 28 is actuated by pressing the activator 28 into the interior of the outer storage container housing 12 at the proximate end 38 towards the compressed gas canister 14. This pushes the compressed gas canister 14 against the piercing end 22 of the gas supply line 18, which pierces the compressed gas canister 14 and causes pressurized gas to flow into the inside of the outer storage container housing 12. This flow of pressurized gas may also be accomplished with a valve instead of a piercing connection to the canister 14. The pressurized gas flows throughout the outer storage container housing 12, both outside the gas supply line 18 and within the gas supply line 18. The pressurized gas outside of the gas supply line 18 causes the piston 24 is to move in the longitudinal direction 20 toward the distal end 36 of the outer storage container housing 12, which drives the piston 24 in the longitudinal direction 20 toward the distal end 36. The movement of the piston 24 pushes the inflatable balloon 16 (wound blocking content(s)) out of the outer storage container housing 12 at the distal end 36 through physically pushing with direct or indirect contact with the inflatable balloon 16 (or wound blocking content(s)) and/or through causing the air between the piston 24 and the inflatable balloon 16 to push the inflatable balloon 16. When the piston 24 finishes its travel and/or reaches the piston stop 26, the piston 24 stops moving and the pressurized gas inside the gas supply line 18 inflates the inflatable balloon 16 outside of the outer storage container housing 12. Optionally, once the piston 24 reaches the intended travel distance the gas flow outside the gas supply line may cease. In this embodiment, the piston stop 26 is arranged at an intermediate position of the device 10 in the longitudinal direction 20, but other positions are within the scope of the present disclosure.

The inflatable balloon 16 includes an optional gauze material 44 that surrounds the inflatable balloon 16, or at least a portion thereof. The gauze material 44 may be configured to provide enhanced clotting ability. For example, the gauze material 44 may be a hemostatic-infused gauze and function as a hemostatic sheath. In some embodiments, a hemostatic powder dispersal mechanism may be utilized to further enhance the mitigation of bleeding from the wound 40, shown in FIG. 3, by applying hemostatic powder 46 to the wound 40, shown in FIG. 3, before inflation of the inflatable balloon 16. For example, the hemostatic powder 46 may be deposited on the inflatable balloon 16, i.e., wound blocking contents, so that the hemostatic powder is dispersed into the wound 40 when the inflatable balloon 16 is expelled from the outer storage container housing 12. The hemostatic powder 46 may be sprayed into the wound 40 cavity, shown in FIG. 3, by pressing the hemostatic powder 46 through a mesh during expulsion. The un-inflated balloon 16 is then pressed into the wound 40 by the continued motion of the piston 24 and the balloon 16 begins to inflate in the wound 40 once the piston 24 reaches the end of its travel at the piston stop 26 or substantially proximate thereto, as discussed above. The inflatable balloon 16 is inflated inside the hemostatic sheath (if equipped) and inflates to fill the wound cavity 40, thereby applying pressure to the entire area contacted by the inflatable balloon 16. In this embodiment, the piston stop 26 is arranged at the distal end 36 of the device 10.

In some embodiments, the wound blocking content(s) 16 comprises gauze, antibiotic agents, hemostatic material and/or powder for wound treatment, or any combination thereof in conjunction with the inflatable balloon, or used independently. Additionally, while the activator 28 is shown in the form of a button in FIGS. 1 and 2, other activation mechanisms are within the scope of the present disclosure. For example, and without limitation, the activator 28 may be a switch, diaphragm, knob, slider or electronic assembly configured to activate the bleeding control device 10 following an input from a user.

Referring to FIG. 3, a schematic illustration of a variant embodiment of the bleeding control device 10 of FIG. 1 is shown in a deployed state in a wound 40 of a patient 42. This embodiment differs from the embodiment of FIG. 1 in that the piston stop 26 is arranged at the distal end 36 of the device 10 instead of at an intermediate position as shown in FIG. 1. The distal end 36 of the outer storage container housing 12 is placed directly into the wound 40 of the patient 42 or substantially proximate thereto by a user, which may be any person operating the bleeding control device 10, including the patient in some circumstances. Then, the user actuates the activator 28. As discussed above, in this embodiment, the activator 28 is actuated by pressing the activator 28 into the interior of the outer storage container housing 12 at the proximate end 38 towards the compressed gas canister 14. This presses the compressed gas canister 14 against the piercing end 22 of the gas supply line 18, shown in FIG. 1, thereby piercing the compressed gas canister 14 and causing pressurized gas to flow into the outer storage container housing 12. The pressurized gas flows throughout the outer storage container housing 12, both outside the gas supply line 18 and within the gas supply line 18. The pressurized gas outside of the gas supply line 18 causes the piston 24 to move toward the distal end 36 and causes the inflatable balloon 16 (the wound blocking content(s)) to exit the outer storage container housing 12 at the distal end 36 and move into the wound 40 of the patient 42. When the piston 24 finishes its travel and/or reaches the piston stop 26, the pressurized gas inside the gas supply line 18 inflates the inflatable balloon 16 to fill the wound 40.

The pressure of the gas delivered from the compressed gas canister 14 is fed into the regulator 30, which at least initially drives the piston 24 to expel some or all of the wound blocking contents 16, including the inflatable balloon, from outer storage container housing 12 and into the wound 40. The pressure driving the piston 24 may, at least initially, be higher than the pressure inflating the inflatable balloon 16 to ensure the inflatable balloon (or wound blocking contents) 16 are ejected from the outer storage container housing 12. As the inflatable balloon 16 inflates, the inflatable balloon 16 fills the cavity of the wound 40. The regulator 30 can be adjusted through the adjustable control 32 to increase or decrease the pressure in the inflatable balloon 16 if the desired outcome is not being achieved. For example, the pressure may be increased if the wound blocking contents 16 is not sufficiently sealing the wound 40 or may be decreased if it appears that the inflatable balloon is overinflated relative to the cavity of the wound 40. The regulator 30 may have a plurality of different discrete pressure level settings of inflation pressure and may initially be set to its lowest pressure level setting and then increased depending on the pressure required to stop bleeding or a desired pressure is reached. The regulator 30 may also serve to keep the inflatable balloon 16 at a given or steady inflation level once inflated so as to not over-pressurize or under-pressurize the inflatable balloon 16. If the pressure is not sufficient to staunch the bleeding, a user may manually select to increase the regulator 30 setting through the adjustable control 32 to the next pressure level setting to further pressurize the balloon 16 to achieve the desired result.

While the compressed gas canister 14 has been described herein as being filled with gas, other materials or substances configured to be stored under pressure are within the scope of the present disclosure. For example, and without limitation, the compressed gas canister 14 may be charged with carbon dioxide, oxygen, nitrogen, argon, and/or water. While the gas supply line 18 is shown as a single piece rigid tube, it is within the scope of the present disclosure for the gas supply line 18 to be a plurality of rigid tubes (i.e. multi-piece), or a flexible tubing, or any combination thereof. For example, the gas supply line 18 could be a single rigid tube connected to flexible tubing(s) or a plurality of rigid tubes connected to flexible tubing(s).

Referring to FIG. 4, a bleeding control device 48 according to another embodiment comprising an alternative wound blocking contents 16 is shown in a deployed state. Elements with like reference numerals to elements discussed above in connection with FIGS. 1-3 are the same and will not be discussed in further detail. In this second embodiment, the wound blocking contents 16 are in the form of packed gauze 50. The piston 24 forces the packed gauze 50 out of the outer storage container housing 12 into or around the wound 40. As the gauze 50 exits the outer storage container housing 12 at the distal end 36, the gauze 50 spreads out to cover the wound 40, thereby controlling and/or blocking bleeding from the wound 40. As with the wound blocking contents discussed above, the gauze 50 may be embedded with a hemostatic agent or powder to provide a faster alternative than manual wound packing while providing a similar result.

Referring to FIG. 5, a bleeding control device 52 is shown in accordance with another embodiment of the present disclosure. Elements with like reference numerals to elements discussed above in connection with FIGS. 1-4 are the same and will not be discussed in further detail. In this third embodiment, the bleeding control device 52 includes a spring deployment system for deploying the wound blocking contents 16 instead of the compressed gas delivery system discussed above. The spring deployment system comprises a spring 54, or other similar resilient member, that is configured to drive the wound blocking contents 16 from the distal end 36 of the outer storage container housing 12 when activated by the activator 28. The spring 54 is in a compressed state when the device 52 is in a non-deployed state, and expands to a non-compressed state (or less compressed state) when the device 52 is activated by the activator 28 to deploy the wound blocking content(s) 16 as the device 52 transitions to a deployed state. The choice between the spring deployment system and the compressed gas delivery system may be based on the deployment and/or reliability characteristics desired in the resulting bleeding control device.

Referring to FIG. 6, a bleeding control device 56 is shown in accordance with another embodiment of the present disclosure. Elements with like reference numerals to elements discussed above in connection with FIGS. 1-5 are the same and will not be discussed in further detail. The bleeding control device 56 includes the spring deployment system discussed above in connection with FIG. 5 to deploy the wound blocking contents 16 from the outer storage container housing 12. In the embodiment shown in FIG. 6, the wound blocking contents 16 is the inflatable balloon 16 as in FIGS. 1-3. In this embodiment, the compressed gas canister 14 inflates the inflatable balloon 16 only when the bleeding control device 56 is activated, but does not provide the driving force for driving the piston 24 to force the wound blocking contents 16 from the distal end 36 of the outer storage container housing 12 of the bleeding control device 56. Actuation of the activator 28 may simultaneously (or substantially simultaneously) activate both the spring 54 of the spring deployment system and the compressed gas canister 14. Alternatively, the bleeding control device 56 may include separate activators 28 for the spring 54 and compressed gas canister 14. As discussed in the embodiments above, once the inflatable balloon 16 is deployed, a regulator 30 may control pressure from the compressed gas canister 14 to inflate the inflatable balloon 16 to the desired pressure and/or to maintain the pressure, for example, within predetermined upper and lower pressure limits.

Figure 7B:
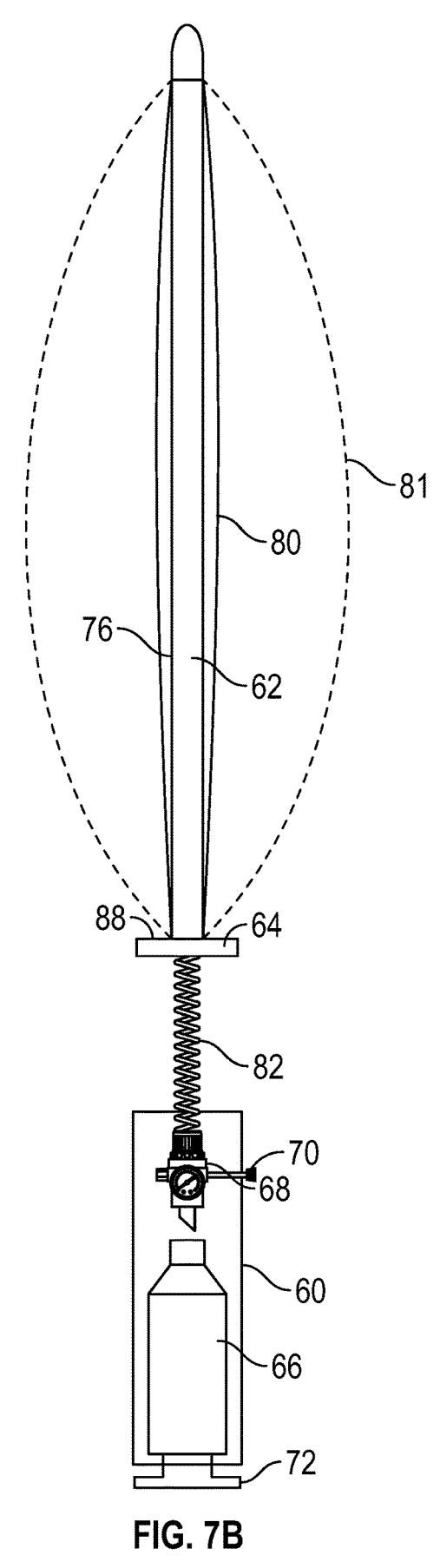
FIG. 7B is an illustration of the bleeding control device of FIG. 7A with the detachable base detached from the canister housing in accordance with the present disclosure.

Referring to FIGS. 7A and 7B, a bleeding control device 58 is shown in accordance with an embodiment of the present disclosure. The device 58 comprises a canister housing 60 connected to a rigid tube 62 through an optional detachable base 64. The detachable base 64 is configured to detach from the canister housing 60. The canister housing 60 includes a compressed gas canister 66 having an optional regulator 68 and adjustable control 70. The compressed gas canister 66 is configured to be activated by an activator 72. The rigid tube 62 extends in a longitudinal direction 74 and includes a pliable tip 76 at a distal end 78 within an inflatable balloon 80. The compressed gas canister 66 is fluidly connected to the inflatable balloon 80 through flexible tubing 82 and is configured to inflate the inflatable balloon 80 when activated by the activator 72. While the tube 62 is described as being a rigid tube, virtually all degrees of rigidity of tubes are within the scope of the present disclosure. Further, the rigid tube 62 may be hollow or solid. Additionally, the bleeding control device 58 may optionally include a cap and/or sleeve (not shown) configured to cover the balloon 80 and rigid tube 62 when the bleeding control device 58 is in the non-deployed state to protect the balloon 80 and/or rigid tube 62 from damage and/or contamination before insertion into a wound. In FIG. 7B, the bleeding control device 58 is shown with the detachable base 64 detached from the canister housing 60 and with broken lines 81 indicating a shape and size of the inflatable balloon 80 when under pressure in an inflated state. Even when detached, the pressure of the inflatable balloon 80 may be controlled via adjustment of the adjustable control 70, thereby controlling the pressure in the inflatable balloon 80 through the flexible tubing 82. While the broken lines 81 show a particular shape and size of the balloon 80 in the inflated state, it is within the scope of the present disclosure for the balloon 80 to be configured to inflate to a different shape and/or size as desired.

In operation, the optional cap (not shown) is removed from the device 58 before use, if so equipped. The bleeding control device 58 may then be inserted into a wound, distal end 78 first, through an optional guide/limiter 84 that prevents the balloon 80 from further widening the entry point of the wound. The optional guide/limiter 84 defines a through-cavity 86 that is sized to receive the balloon 80 and rigid tube 62 when the inflatable balloon 80 is not inflated. The bleeding control device 58 may be inserted to a desired depth and/or until the user inserting the device 58 feels a sufficient amount of resistance. For example, the bleeding control device 58 may be inserted until met with resistance from a bullet (or other foreign object) where the bullet (or other foreign object) is still in the patient, or may be inserted to a desired depth or until met with resistance from the bottom of a wound cavity when no bullet or foreign object is present in the patient, such as for a stab or puncture injury. The balloon 80 may optionally be marked with longitudinal measurements in the longitudinal direction 74 to indicate the depth of the wound cavity when inserted into a patient. The maximum pressure may be limited to avoid causing further damage. Once the bleeding control device 58 is positioned in the wound, the activator 72 is actuated to activate the compressed gas canister 66, thereby causing pressurized gas to flow through the flexible tubing 82 and into the inflatable balloon 80 to inflate the inflatable balloon 80. The inflation of the inflatable balloon 80 applies pressure to the wound to mitigate bleeding until the patient can receive appropriate and more thorough medical care.

Once the inflatable balloon 80 has been inflated in the wound cavity, the canister housing 60 may be detached via the detachable base 64 and may be positioned away from the wound. For example, the canister housing 60 may be arranged flat against the body and secured to the patient or the patient's clothing by a hook and loop type fastener, adhesive, tape, or any similar fastening mechanism. The rigid tube 62 could then also be removed, if desired, with a gasket material 88 preventing gas from escaping from the balloon 80 through the opening where the rigid tube 62 was arranged. The rod 62 and tubing 82 may be offset so the removal of one does not affect the other. The rigid tube 62 can also be removed at any time after inflation without the base 64 being detached from the body 60. The regulator 68 may be configured for maintaining the desired pressure level within the balloon 80 and, therefore, would replenish gas lost due to an imperfect seal by the gasket material or gland 88, or any unintended perforations of the balloon if necessary. Once the gas cylinder is relocated against the body of the patient, additional bandages may be wrapped around the wound to provide additional pressure and/or clotting assistance.

Advantageously, the device 58 having the detachable base 64 being configured to detach from the canister housing 60 allows for the canister housing 60 to become detached such that the canister housing 60 may be laid down and secured to the patient's body, thereby reducing length of the device 58 protruding from the patient in the longitudinal direction 74. This reduction in length reduces the potential for interference by the device 58 with first responders and/or medical professionals while attending to the needs of the patient. The reduction in length may decrease the likelihood of the balloon 80 being jostled or dislodged by contact with a person or object. In some embodiments, for an even greater reduction in length and reduction of potential interference, the rigid tube 62 and/or gas supply line 82 is optionally removable from the inflatable balloon 80. The inflatable balloon 80 may include the gasket 88 (or self-sealing grommet or valve) to prevent loss of pressure of the inflatable balloon 80 after removal of the rigid tube 62 and/or gas supply line 82.

Advantageously, the device 58 allows for mitigating the bleeding of wounds having relatively narrow entry points due to the configuration of the inflatable balloon 80 around the rigid tube 62. For example, the device 58 may be configured to address bleeding stemming from a wound caused by a common military rifle caliber, such as 5.56 mm or 7.62 mm, which may have a potentially more narrow entry point opening compared to handgun wound entry point openings. However, since the inflatable balloon 80 inflates to fill the wound cavity, this embodiment is also applicable for use with larger wounds and/or larger entry point openings.

In some embodiments, the device 58 is configured such that the inflatable balloon 80 inflates at different rates and/or inflates to different widths. For example, the balloon 80 may be configured with a progressive thickness so that a first portion of the balloon 80 near the distal end 78 inflates before a second portion of the balloon 80 further from the distal end 78 than the first portion in the longitudinal direction 74 (e.g. a second portion nearest the canister housing 60), and/or inflates to a different size and/or shape in order to provide a different applied pressures at different regions of the balloon 80 in the longitudinal direction 74. A balloon 80 configured in this manner may control bleeding by first filling a distal gap in an exit wound opening, or in the case of a wound without an exit, the wound portion furthest from the entry wound, which may be larger than an entry wound opening to avoid opening the entry wound further and/or by applying more/less pressure at one portion of the wound relative to another portion of the wound because of the predetermined shape of the balloon 80.

Figure 8:
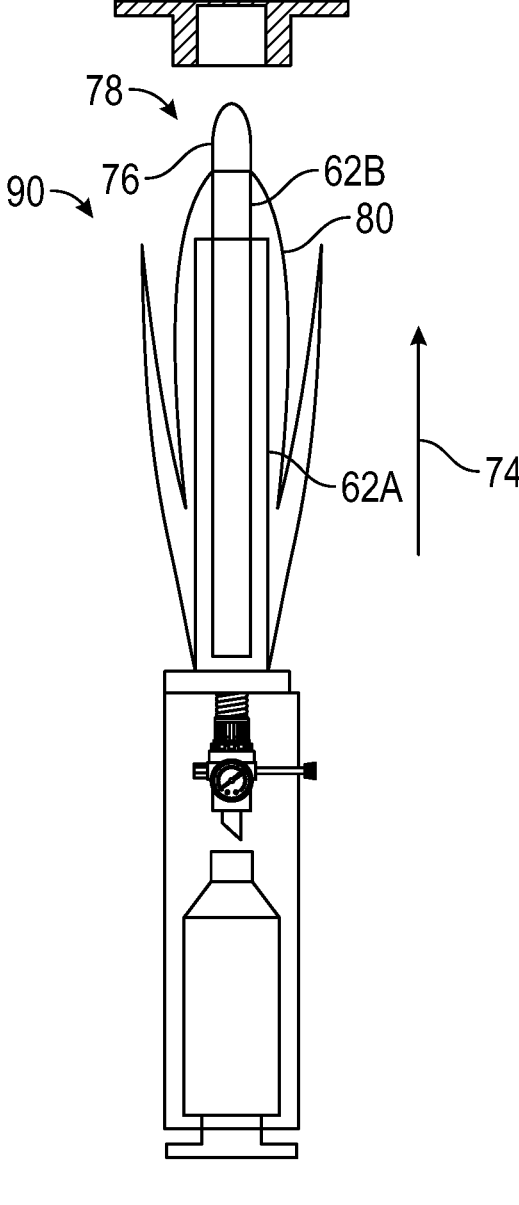
FIG. 8 is an illustration of a bleeding control device in a non-deployed state in accordance with the present disclosure.

Referring to FIG. 8, a bleeding control device 90 is shown in accordance with the present disclosure. The device 90 is similar in structure and use to the device 58 of FIG. 7. Elements with like reference numerals to elements discussed above in connection with FIGS. 1-7 are the same and will not be discussed in further detail. In this embodiment, there is a multi-piece tube or rod structure comprising an outer tube 62A and an inner tube (or rod) 62B. The inner tube 62B includes a pliable tip 76 at a distal end 78. The difference in use is that once the cap was removed the top of the balloon 80 may be loosely tethered to the cap to extend the inner tube 62B to full length or the user could manually extend the balloon 80 (preferably with a gloved hand) by withdrawing the inner tube 62B from the outer tube 62A in a longitudinal direction 74. The tube may have a protrusion that locks the tube (or rod) 62A in place to prevent the tube (or rod) 62A from being collapsed once extended. The remainder of the use is the same as the description above. Advantageously, this embodiment may provide a more compact package to facilitate the carrying and/or storage of the device 90 when not in use. In some embodiments, the length of the outer tube 62A and inner tube (or rod) 62B is for instance, 6-8 inches in length in the longitudinal direction 74 when in the collapsed condition, but 12 inches in length when fully extended. However, other lengths (in both the collapsed and fully extended conditions) are within the scope of the present disclosure. For example, in the collapsed condition the length of the outer tube 62A and inner tube (or rod) 62B may be 4 inches in length in the longitudinal direction 74.

Figure 9:
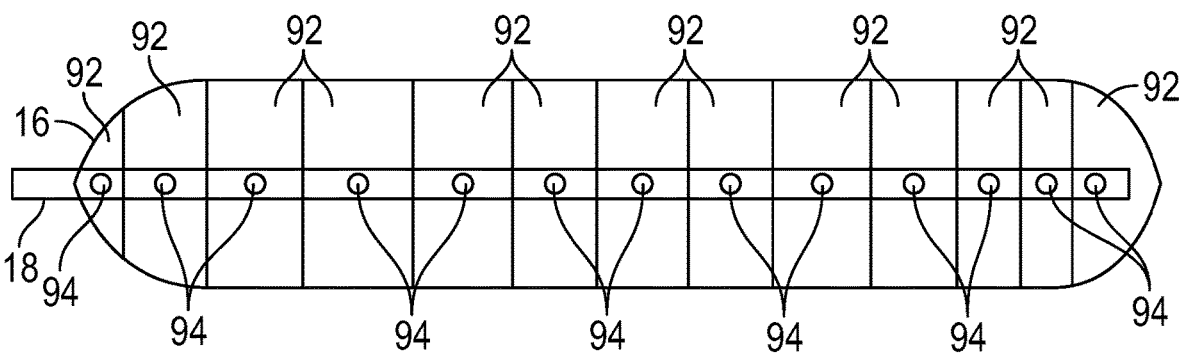
FIG. 9 shows a bleeding control device balloon and gas supply line in accordance with the present disclosure.

Referring to FIG. 9, an inflatable balloon 16 and gas supply line (or inflation rod) 18 of a bleeding control device is shown in accordance with the present disclosure. The inflatable balloon 16 is a multi-chamber balloon that includes a plurality of chambers 92 from the proximal end to distal end. The gas supply line 18 includes a plurality of holes 94 that may each optionally be equipped with a one-way valve. When manufacturing the device, the spacing of the chambers 92 and/or holes 94 may be selected based on a desired size and spacing for inflating the balloon 16. For example and without limitation, the spacing of each chamber 92 in the longitudinal direction from the proximal end to the distal end may be 1 cm. The gas supply line 18 may be used with balloons 16 having the multi-chamber configuration as shown, or with balloons having only one chamber for providing quick and even pressure application.

Figure 10:
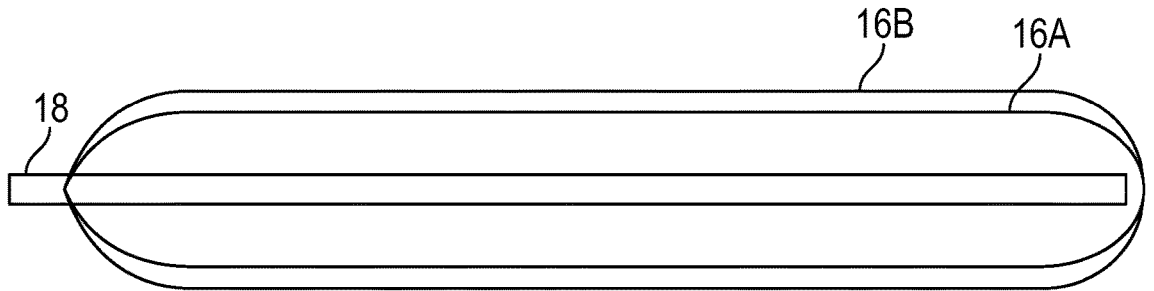
FIG. 10 shows a bleeding control device inner balloon, outer balloon and gas supply line in accordance with the present disclosure.

Referring to FIG. 10, an inner inflatable balloon 16A and outer inflatable balloon 16B with gas supply line (or inflation rod) 18 of a bleeding control device is shown in accordance with the present disclosure. The balloons 16A, 16B are configured to assist with insertion by utilizing different material properties, or limit free expansion. For example, in some embodiments the material of the inner inflatable balloon 16A is different from the material of the outer inflatable balloon 16B (or at least different in weight % of their composition of elements). In some embodiments, the inner balloon 16A is less compliant and inflated to a predetermined size and the outer balloon 16B inflates with a lower pressure to fill voids left by the less compliant inner balloon 16A. The outer balloon 16B may serve to protect the patient from being exposed to the inner balloon 16A or exposed to inner balloon 16A fragments should the inner balloon 16A burst or rupture, thereby preventing contamination of the patient body from the inner balloon 16A. In some embodiments, the outer inflatable balloon 16B is not fluidly connected to any inflation means. In other words, the outer inflatable balloon 16B is inflated by virtue of the inner inflatable balloon 16A, which is fluidly connected to an inflation means (e.g. a compressed gas canister or hand pump), being inflated.

Figure 11:
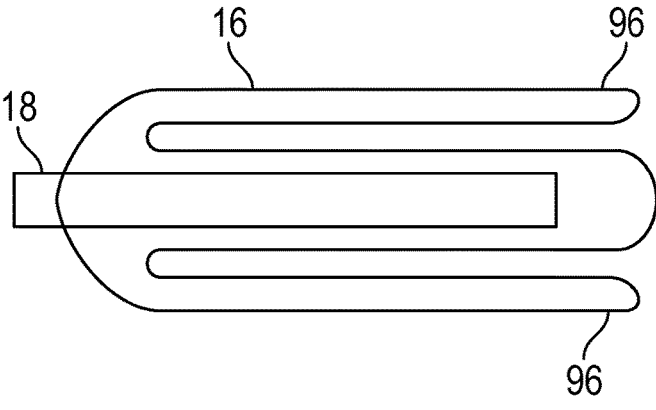
FIG. 11 shows a bleeding control device balloon and gas supply line in accordance with the present disclosure.

Referring to FIG. 11, an inflatable balloon 16 and gas supply line (or inflation rod) 18 of a bleeding control device is shown in accordance with the present disclosure. The inflatable balloon 16 is folded inside itself so inflation will extend along into a wound channel (e.g. in channel of wound 40 in FIG. 3). The balloon 16 is folded inside itself such that there is at least one doubled over folded length 96 of balloon 16. This unfurling balloon 16 allows for shorter gas supply line 18 length in the longitudinal direction from the proximal end to the distal end.

Figure 12A:
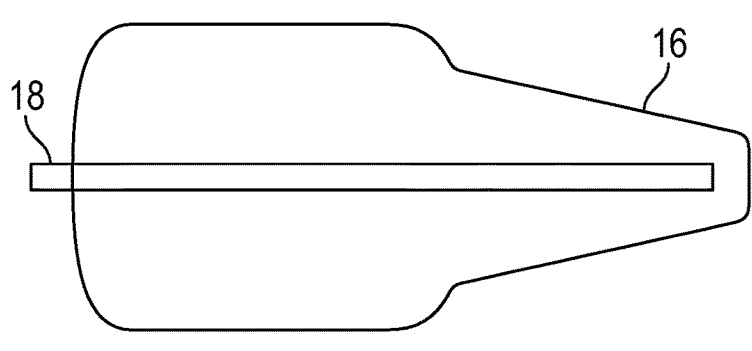
FIG. 12A shows bleeding control device balloon and gas supply line in accordance with the present disclosure.
Figure 12B:
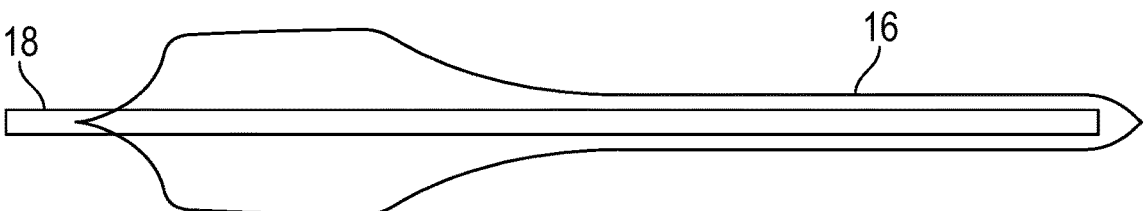
FIG. 12B shows bleeding control device balloon and gas supply line in accordance with the present disclosure.
Figure 12C:
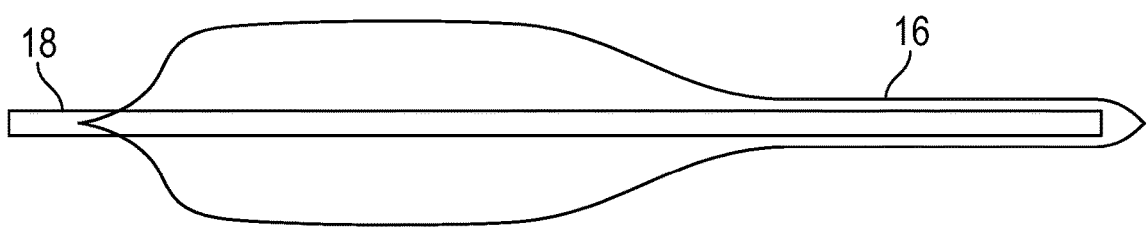
FIG. 12C shows bleeding control device balloon and gas supply line in accordance with the present disclosure.

Referring to FIGS. 12A-12C, inflatable balloons 16 and gas supply lines (or inflation rods) 18 for a bleeding control device are shown with the balloons 16 selectively shaped for treating different firearm projectile wounds. The balloon 16 shown in FIG. 12A is shaped for treating a shotgun-type projectile wound. The balloon 16 shown in FIG. 12B is shaped for treating a pistol-type projectile wound. The balloon 16 shown in FIG. 12C is shaped for treating a rifle-type projectile wound. In some embodiments, the bleeding control device is configured to have the balloon 16 interchangeable so that the balloon type/shape of choice is selected by the user and installed or attached to the device prior to inflation. Thus, the user can change the balloon 16 to a balloon type of a desired shape for controlling the bleeding of a corresponding wound type or shape as is needed or desired.

Figure 13:
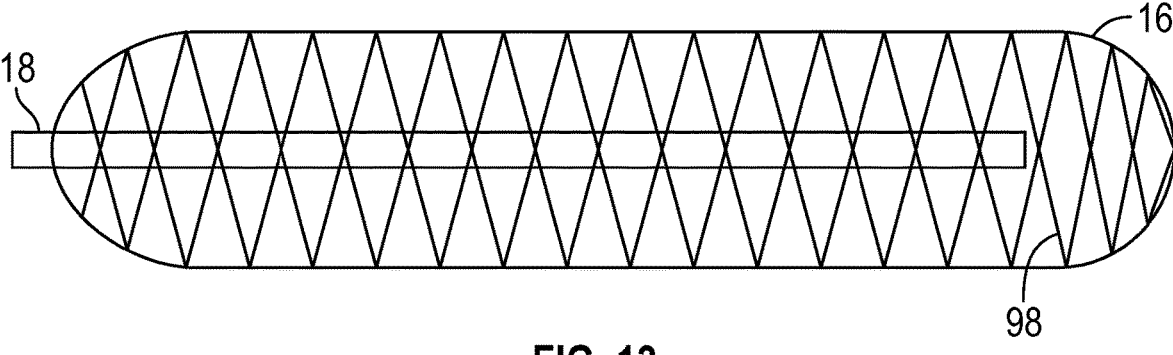
FIG. 13 shows a bleeding control device balloon and gas supply line in accordance with the present disclosure.

Referring to FIG. 13, an inflatable balloon 16 and gas supply line (or inflation rod) 18 of a bleeding control device is shown in accordance with the present disclosure. The inflatable balloon 16 is provided with a mesh 98 configured to limit runaway inflation of the balloon 16. The mesh 98 can be arranged externally and/or internally of the balloon 16 material. The mesh 98 ensures that the balloon 16 does not inflate beyond a predetermined size and/or shape should there be a malfunction or user error of the canister gas or valve/regulator operation. In some embodiments, in lieu of, or in addition to, a coating on the balloon 16 is provided to limit runaway inflation. In some embodiments, the coating is instead additional thickness of the balloon 16 material (e.g. plastic mesh, synthetic rubber, etc.). In some embodiments, the additional material or coating is configured to have a higher durometer rating than the balloon 16 material itself.

Figure 14:
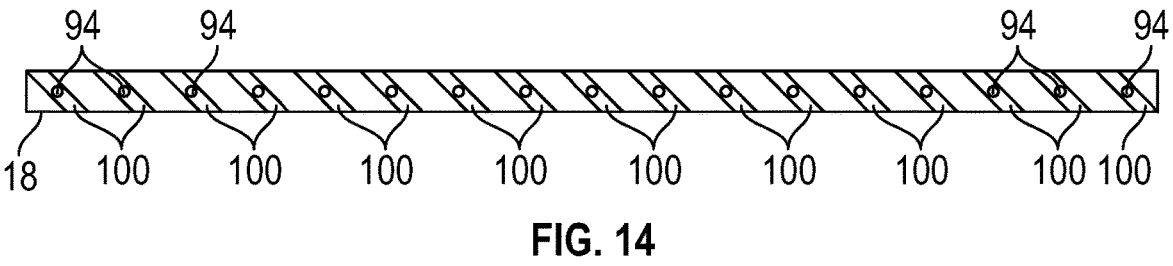
FIG. 14 shows a bleeding control device gas supply line (or inflation rod) in accordance with the present disclosure.

Referring to FIG. 14, a gas supply line (or inflation rod) 18 of a bleeding control device is shown in accordance with the present disclosure. The gas supply line 18, like the embodiment shown in FIG. 9, includes a plurality of holes 94 for delivering the gas for inflating an inflatable balloon. In this embodiment, the holes 94 are arranged at recessed grooves 100 in the gas supply line 18. The recessed grooves 100 assist in ensuring prompt and reliable balloon inflation should some of the holes 94 be covered by balloon material or other obstruction (e.g. hemostatic material, powders, other medical materials). The grooves 100 are spirally arranged. In some embodiments, the grooves 100 are a single groove 100 spirally extending along the length of the gas supply line 18.

Figure 15A:
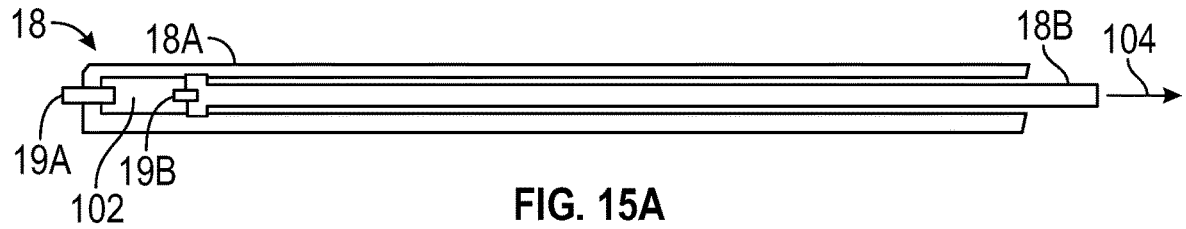
FIG. 15A shows a bleeding control device gas supply line in accordance with the present disclosure.

Referring to FIG. 15A, a gas supply line (or inflation rod) 18 of a bleeding control device is shown in accordance with the present disclosure. The gas supply line 18 includes a first part 18A and a second part 18B movable within the first part 18A. The first part 18A includes a first port 19A that fluidly connects the canister gas to an inner volume 102. When activated, the gas moving through the first port 19A enters the inner volume 102 and presses on the second part 18B to move the second part 18B in the extending direction 104 in a telescoping manner. The second part 18B includes a second port 19B that allows the gas to move through the second part 18B and out of the second part 18B for filling an inflatable balloon. Thus, when not in use, the second part 18B can be compactly stored within the first part 18A and then automatically extended to an extended position with the same canister gas that ultimately pressurizes and inflates the inflatable balloon of the bleeding control device.

Figure 15B:
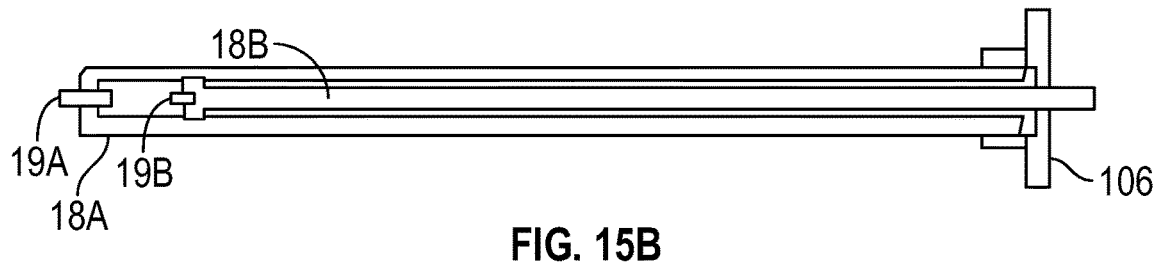
FIG. 15B shows a bleeding control device gas supply line in accordance with the present disclosure.

Referring to FIG. 15B, a gas supply line (or inflation rod) 18 of a bleeding control device is shown in accordance with the present disclosure, which is substantially similar to the embodiment shown in FIG. 15A except that a contact switch 106 is provided. Upon actuation, for example with contact with a patient, the contact switch 106 is configured to cause at least a portion of the gas supply line (inflation rod) 18 to extend away from the housing. The contact switch 106 can be cause the gas supply line 18 portion to extend with pressure from the gas canister. In some embodiments, the contact switch 106 is configured to release spring pressure to extend the inflation rod 18. The contact switch 106 may also be configured to act as an interlock so the balloon is not inflated outside of the wound or patient's body. Advantageously, the use of a contact switch 106 to cause extension of the inflation rod instead of requiring a user to perform one or more steps makes operation and use of the bleeding control device automatic, and the reduction of steps to extend the rod can lead to reduced activation times that may be useful and/or needed while the patient is bleeding.

Figure 15C:
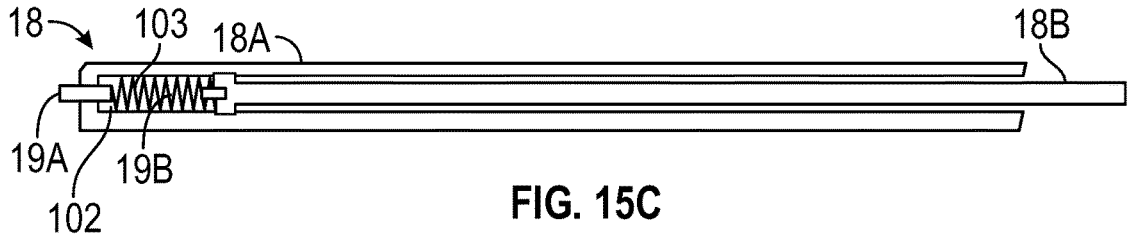
FIG. 15C shows a bleeding control device gas supply line in accordance with the present disclosure.

Referring to FIG. 15C a gas supply line (or inflation rod) 18 of a bleeding control device is shown in accordance with the present disclosure. The gas supply line 18 is similar to the embodiment shown in FIG. 15A except that a spring 103 is arranged within the inner volume 102 and assists extending the second part 18B in the extending direction 104 (FIG. 15A) with a spring force generated by the spring 103. Thus, inflation rod 18 extends with a combination of gas force and spring force for moving the second part 18 to the extended position.

Figure 15D:
FIG. 15D shows a bleeding control device gas supply line in accordance with the present disclosure.

Referring to FIG. 15D a gas supply line (or inflation rod) 18 of a bleeding control device is shown in accordance with the present disclosure. The gas supply line 18 is similar to the embodiment shown in FIGS. 15B and 15C. A spring 103 is arranged within the inner volume 102 and assists with extending the second part 18B in the extending direction 104 (FIG. 15A). A contact switch 106 is arranged to cause the gas and spring force to release and/or move the second part 18B to the extended position and/or in the extending direction 104.

Figure 16A:
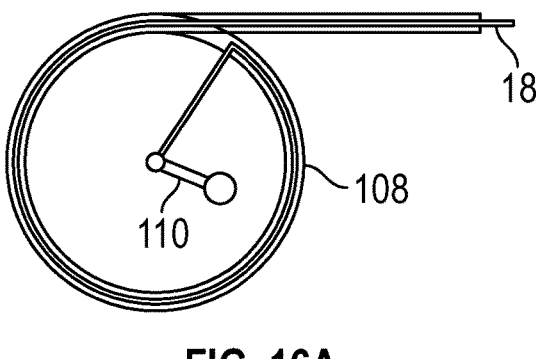
FIG. 16A shows a bleeding control device gas supply line and case in a stored position in accordance with the present disclosure.
Figure 16B:
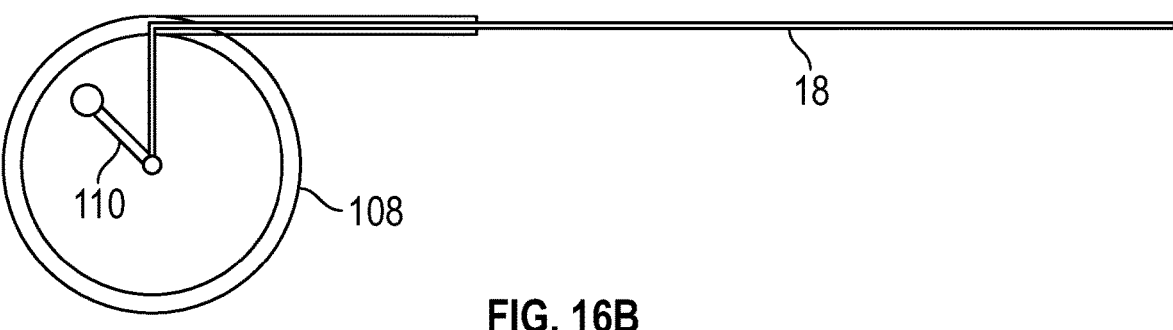
FIG. 16B shows the bleeding control device gas supply line and case of FIG. 16A in an extended position in accordance with the present disclosure.

Referring to FIGS. 16A and 16B, a gas supply line (or inflation rod) 18 with case 108 of a bleeding control device is shown in accordance with the present disclosure. The gas supply line 18 is arranged to be extended from a stored position within the case 108 shown in FIG. 16A to an extended position shown in FIG. 16B through a rotatory motion with a rotary element 110 of the case 108. Thus, when not in use, the gas supply line 18 is compactly stored within the case 108 in a circular-shaped storage position. When deployed to the desired length, the gas supply line 18 can be activated through any of the disclosed structures/methods disclosed herein for inflating an inflatable balloon.

Referring to FIG. 16C, a gas supply line (or inflation rod) 18 with case 108 of a bleeding control device is shown in accordance with the present disclosure that is similar to the embodiment shown in FIGS. 16A and 16B except that a contact switch 106 is provided that is configured to cause extension of the gas supply line 18 through a spring mechanism arranged in the case 108 upon actuation (e.g. upon pressing upon the patient's body).

Referring to FIG. 17, an inflatable balloon 16 and gas supply line (or inflation rod) 18 of a bleeding control device is shown in accordance with the present disclosure. The inflatable balloon 16 is compressed such that upon inflation the balloon 16 forces the second part 18B of the inflation rod 18 to extend in the extending direction 104 relative to the first part 18A. Inflation of the inflation rod 18 may be independent or share an inflation connection with the balloon 16.

Referring to FIG. 18, an inflatable balloon 16 and gas supply line (or inflation rod) 18 of a bleeding control device is shown in accordance with the present disclosure. The balloon 16 includes a tubing 111 along a length of the balloon 16. The tubing 110 is configured to relieve pressure for lung injuries with a one-way valve 112 arranged at or near a proximal end of the tubing 111. The one-way valve 112 allows air/gas out of the lung or chest cavity of the patient, but not in. The tubing 110 may define a single opening 114 to allow entrance of air/gas into the tubing 111 for removal through the one-way valve 112, or there may be a plurality of openings 114, e.g. at or near the distal end of the tubing 110 or dispersed throughout the length of the tubing 111.

Referring to FIG. 19, a bleeding control device 10 is shown in accordance with the present disclosure (inflatable balloon not shown for simplicity). The device 10 comprises a housing 12 that includes a transmitter 116, a battery 118, an antenna 120 and/or a signal light 122. The transmitter 116 and/or the light 122 are configured to become activated upon activation of gas canister 14 (or upon activation manually) in order to assist rescue workers finding the patient by way of locating the bleeding control device. In some embodiments, the light 122 requires separate activation (e.g.

through separate button or switch) so that the light 122 is only activated when desired, which may be beneficial during an active shooter situation where the victim/patient does not want to give away their position to the shooter. A rescue worker can use a remote device to determine signal strength and/or direction of the transmitter to assist in locating a patient in a nearby environment. In some embodiments, the transmitter 116 is GPS-enabled in order to provide a precise location to rescues workers wirelessly. In some embodiments, the light 122 is configured to activate with a strobe effect to assist rescue workers in locating the device/patient.

In some embodiments, the transmitter 116 is configured to transmit to the nearest 911 call center (or other emergency resource center) using a cellular network or other communication means (e.g. satellite/internet etc., or similar to EPIRB system registration networks). The transmitter 116 indicating activation of a bleeding control device 10 along with location information/data advantageously may reduce the emergency response time for reaching a patient and providing urgent care. The location information/data provided by the transmitter 116 can be encrypted and/or sent with spread spectrum for military applications to avoid disclosing user location to enemies. The bleeding control device 10 may send an initial message first without location information and wait to send any message until after receiving an authorization or confirmation return message/signal from an authorized medic or response unit. In military applications, the device may be configured to not transmit until a valid signal is first received from the authorized medic or response unit, or is instructed to begin transmitting by the medic/response unit.

Figure 20:
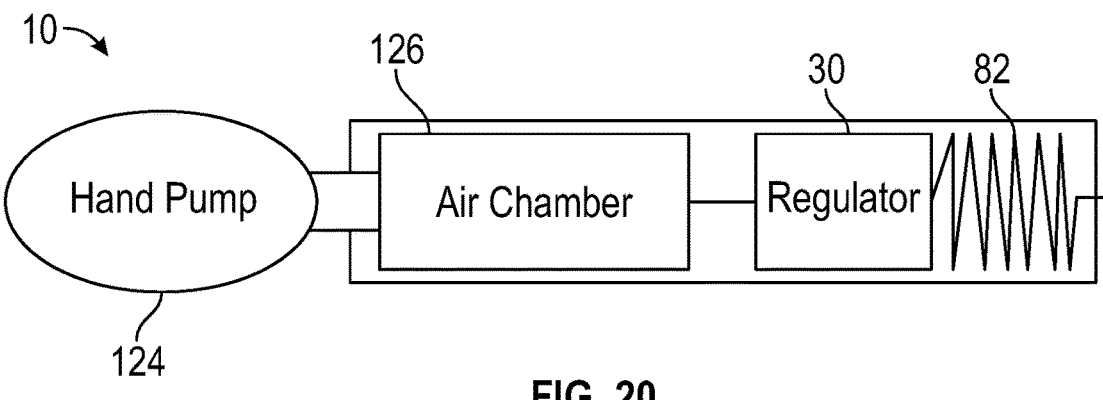
FIG. 20 shows a bleeding control device in accordance with the present disclosure.

Referring to FIG. 20, a bleeding control device 10 is shown in accordance with the present disclosure (inflatable balloon not shown for simplicity). The device 10 includes a manual hand pump 124 fluidly connected to an air chamber 126 within a container housing 12. The air chamber 126 is fluidly connected to a regulator 30 for regulating the air pressure to an inflatable balloon through flexible tubing 82. In operation, a user/patient can manually squeeze the hand pump 124 (e.g. a squeeze bulb, linear, or any other human powered pump) for providing air pressure to the air chamber 126 and then to the regulator 30 for inflating the inflatable balloon or to maintain pressure in the balloon (e.g. after a period of time if the balloon lost any pressure). The regulator 30 also serves to relieve or reduce pressure if the detected pressure becomes too high (e.g. due to body movement, gas expansion due to heating from body heat, etc.).

Figure 21:
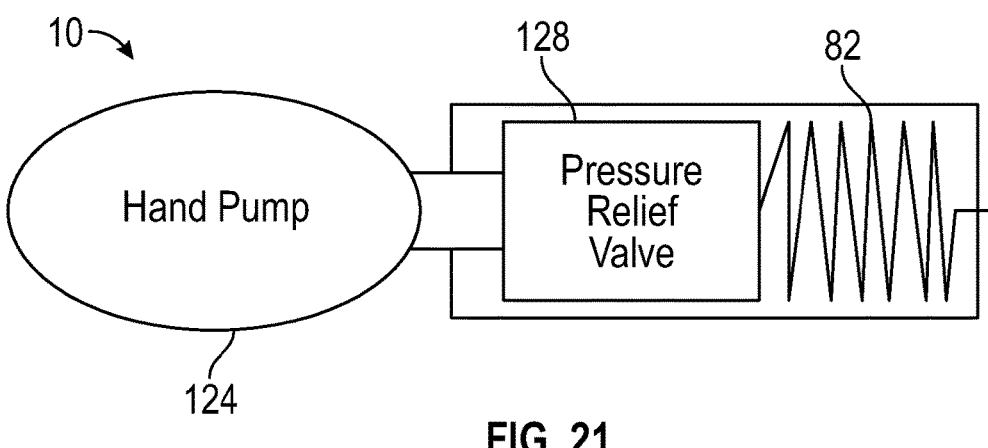
FIG. 21 shows a bleeding control device in accordance with the present disclosure.

Referring to FIG. 21, a bleeding control device 10 is shown in accordance with the present disclosure (inflatable balloon not shown for simplicity). The device 10 includes a manual hand pump 124 fluidly connected to a pressure relief valve 128 that is configured to allow inflation of the inflatable balloon but prevent overinflation beyond a predetermined inflation pressure.

Figure 22:
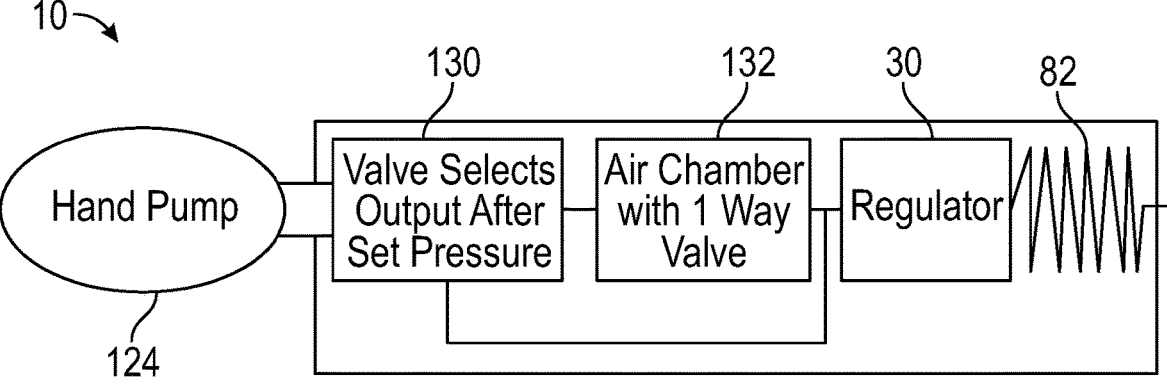
FIG. 22 shows a bleeding control device in accordance with the present disclosure.

Referring to FIG. 22, a bleeding control device 10 is shown in accordance with the present disclosure (inflatable balloon not shown for simplicity). The device 10 includes a manual hand pump 124 fluidly connected to a automatic selector valve 130 within a container housing 12. The automatic selector valve 130 allows a user to inflate the balloon first with the manual hand pump 124 before pressurizing the air chamber which feeds a regulator 30 for inflating the inflatable balloon through the coiled air line 82, or to an air chamber with one-way valve 132. Thus, in operation, a user can directly inflates an inflatable balloon, then later pressurize the air chamber with one-way valve 132. The one-way valve prevents air from returning from the air chamber 132. The air chamber 132 acts as a pressurized air reservoir to maintain pressure in the inflatable balloon that might otherwise reduce due to leakage from, for example, patient body repositioning. Advantageously, the air chamber 132 allows the user to attend to other tasks instead of repeatedly reinflating the inflatable balloon.

Figures 23, 24, 25:
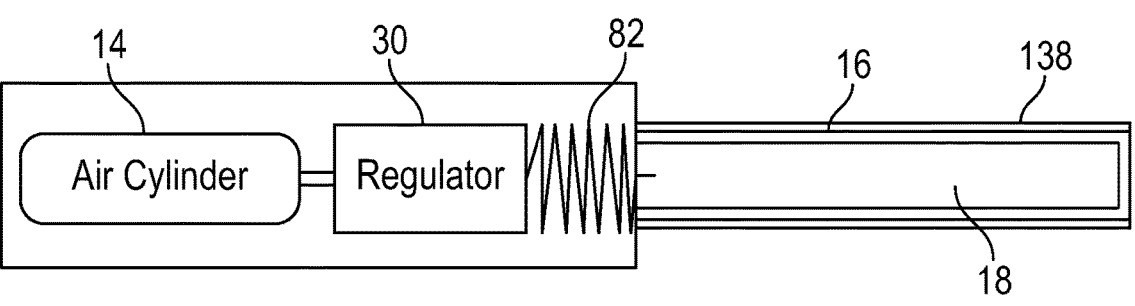
FIG. 23 shows a bleeding control device in accordance with the present disclosure.
FIG. 24 shows a bleeding control device in accordance with the present disclosure.
FIG. 25 shows a bleeding control device in accordance with the present disclosure.

Referring to FIG. 23, a bleeding control device is shown in accordance with the present disclosure (inflatable balloon not shown for simplicity). The device includes a compressed gas canister 14 fluidly connected to a regulator 30 for providing inflation pressure to the inflatable balloon through the air line 82. The inflatable balloon can also be inflated (or maintained with pressure) from an external air input source connection through the provided Luer lock connection 134. The external air source can be provided from, for example, a pressure source arranged in an ambulance or hospital setting. In some embodiments, the Luer lock connection 134 can be other air connection type fittings such as, for example, a quick connect/disconnect fitting that is configured to mate with an air injection hose in an ambulance or hospital setting.

Referring to FIG. 24, a bleeding control device 10 is shown in accordance with the present disclosure. The device 10 includes a housing 12 that includes a transmitter 116, a battery 118, an antenna 120 and a light 122. The device 10 includes a compressed gas cylinder 14 fluidly connected to a regulator 30 that inflates an inflatable balloon 16 through an air line 82. The device 10 further includes a sensor 136 that is configured to sense a pulse of the patient (e.g. a fingertip pulse sensor). In some embodiments, the transmitter 116 is configured to transmit patient pulse data (or information) obtained or derived from the sensor 136 with the GPS location data (e.g. as discussed above in connection with the FIG. 19 embodiment).

Referring to FIG. 25, a bleeding control device 10 is shown in accordance with the present disclosure. The device includes a housing 12 containing a compressed gas canister 14, a regulator 30 and air line 82. The inflatable balloon 16 of the device 10 is sheathed within a sheath 138. The sheath 138 advantageously shields the inflatable balloon 16 from contaminants during shipping and storage times to reduce risk of infection of the patient upon insertion. Thus, the sheath 138 is removed prior to insertion of the inflatable balloon 16 into the patient. In some embodiments, the sheath 138 is a split sheath type that remains with the balloon 16 or device 10 when inserted (e.g. breakaway on all but one point or completely detaches from balloon 16 but a tether to device 10 housing 12). The sheath 138 also assists with protecting the balloon 16 during insertion against bone fragments, bullet pieces or other debris. In some embodiments, the sheath 138 that extends the length of the length of the balloon 16 and is collapsible such that if the inflation rod 18 can only be inserted partially the balloon 16 portion not inside the patient body is prevented from inflating due to the sheath 138 surrounding the outside-the-body balloon 16 portion, thereby preventing the outside-the-body portion of the balloon 16 from inflating. Advantageously, the collapsible sheath 138 allows for dynamic targeted balloon 16 inflation in the case of a shallower wound channel.

Advantageously, bleeding control devices in accordance with the present disclosure may comprise an inflatable balloon, gauze, a hemostatic material or powder for wound treatment, or any combination thereof. In some embodiments, a safety lockout may be provided to prevent accidental discharge. Additionally, all of the wound blocking contents described herein may advantageously include X-Ray contrast material such as a fine metal wire, metalized polyester film embedded in the balloon or other such devices configured to show up on an x-ray in order to alert medical staff to the balloon's or wound blocking contents' presence within the wound.

In use of the various bleeding control devices described herein, an end of the device being used is placed proximate to, or directly into, a wound opening and the actuator button is pressed or actuated. When the actuator button is actuated, the compressed gas canister, potentially filled with CO2, will either be pierced, or otherwise caused to open to direct gas flow within the outer storage container housing. The gas flow may be directed through a regulator that controls the gas flow pressure to drive a piston forward within the outer storage container housing to eject or expel the wound blocking contents out of the end of the device and into and/or around the wound cavity. If bleeding control is pursued quickly and correctly with the various bleeding control devices described herein, bleeding may be quickly controlled until more advanced care and treatment can be obtained.

According to the present disclosure, a bleeding control method comprises providing a bleeding control device, and activating the bleeding control device to deploy wound blocking content(s) contained within an outer storage container housing into a wound of a patient. In some embodiments, the wound blocking content(s) comprise an inflatable balloon, and the method further comprises inflating the inflatable balloon to a predetermined pressure or desired pressure while the inflatable balloon is inside the wound in order to apply sufficient pressure to the wound to stop or reduce bleeding.

In some embodiments, the compressed gas canister may be replaceable with a replacement cartridge compressed gas canister. In other embodiments, the compressed gas canister cannot be replaced and the bleeding control device is a single use device. Alternatively, the bleeding control device may include a compressed gas canister that cannot be replaced, but the compressed gas canister may have enough charge therein for several uses where the wound blocking contents are replaced. In some embodiments, the replacement cartridge compressed gas canister has a threaded portion allowing the compressed gas canister to thread directly with the regulator of the device.

In accordance with the present disclosure, different packaging options are available for the inflatable balloon being disposed within the outer storage container housing. For example, inflatable balloons with different inflation characteristics may be provided to conform to different wound types, such as deep narrow wounds, wide narrow wounds or wounds with distinctive entry wound openings. Moreover, the various bleeding control devices described herein may be configured so that a user can replace the inflatable balloons by attaching them to a gas nozzle in communication with the regulator so that the user can select an appropriate balloon for a specific wound. Any of the inflatable balloon size or shape configurations may be provided with hemostatic-infused gauze surrounding the balloon to encourage clotting by additional means than solely by pressure as discussed above. A powder dispersal mechanism, which could be a plastic mesh and packed powder positioned within the outer storage container housing before the balloon also may be used to spread a clotting agent or any other agent such as, but not limited to, antibacterial agents before applying pressure to the wound with the balloon. In some embodiments, the balloon includes a combined antiseptic/lubrication coating that advantageously reduces risk of infection and assists with inflation and insertion of the balloon into the patient.

All balloon variants of wound blocking contents in accordance with the present disclosure may make use of a regulator, which could be operated to increase or decrease pressure if the desired outcome is not being achieved. The balloon may have a short length of tubing that would allow the body of the device to be laid on top of the patient with the outer container of the device having hook fasteners (similar to the hook side of hook and loop fasteners) to stick to the clothing or bandages of the patient. The regulator may have a deflation setting or could be pierced by hospital staff once the patient arrives at a care facility in order to deflate the inflatable balloon for removal from the wound. All balloon variants may be configured to maintain an inflation and regulation source.

Additionally, in accordance with some embodiments of the present disclosure, z-folded gauze or other absorptive material may be injected into and/or around a wound cavity. The gauze could be packed within the outer storage container housing in a folded state, and unfold in or around the wound cavity once deployed. The gauze may also include an embedded hemostatic agent or powder to more quickly mitigate bleeding compared to traditional manual wound packing. If required, multiple devices may be utilized to complete wound packing and provide an expedited form for tending to a bleeding wound. Additionally, such devices may be used along side a traditional pressure bandage and manual pressure.

In some embodiments according to the present disclosure, a bleeding control device may be used to deploy a powder to a wound. As disclosed herein, the powder could be deployed with additional wound blocking contents, such as a balloon or gauze packing. In the alternative, the storage container could be packed with powder and the pressing of the actuator button deploys a power to the wound cavity. The powder may be hemostatic or a mixture of hemostatic and antibiotic materials or the like.

In some embodiments according to the present disclosure, a bleeding control device may utilize a balloon or balloon sheath coated with a thin layer of antibacterial cream which may assist in insertion and direct application to the balloon areas of contact.

Advantageously, the present disclosure provides bleeding control devices that provide new, optimized and efficient approaches to covering and blocking a wound to control bleeding.

Although various features have been shown in different figures for simplicity, it should be readily apparent to one of skill in the art that various features may be combined without departing from the scope of the present disclosure.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A bleeding control device comprising:
    a housing;
    an inflatable balloon arranged within and/or connected to the housing;

inflation means arranged within and/or connected to the housing;

a gas supply line arranged within and/or connected to the housing; and a transmitter configured to transmit location information of the bleeding control device only after receiving a valid signal from an authorized medic or response unit;

wherein the inflation means is fluidly connected to the inflatable balloon through the gas supply line.

2. The bleeding control device according to claim 1, wherein the inflation means comprises a compressed gas canister.

3. The bleeding control device according to claim 1, wherein the inflation means comprises a hand pump.

4. The bleeding control device according to claim 1, further comprising a pulse sensor connected to the housing, wherein the transmitter is further configured to transmit heart rate data obtained or derived by the pulse sensor.

5. The bleeding control device according to claim 1, further comprising a light connected to the housing, wherein the light is configured to activate upon activation or operation of the inflation means.

6. The bleeding control device according to claim 1, further comprising a mesh arranged on and/or within the inflatable balloon, wherein the mesh is configured to prevent the inflatable balloon from being inflated beyond a predetermined size and/or shape.

7. The bleeding control device according to claim 1, wherein the gas supply line comprises a plurality of holes, wherein the inflation means is fluidly connected to the inflatable balloon through the plurality of holes.

8. The bleeding control device according to claim 7, wherein the gas supply line defines one or more recesses at the plurality of holes.

9. The bleeding control device according to claim 8, wherein the one or more recesses are spirally arranged about the gas supply line.

10. The bleeding control device according to claim 1, further comprising a case with an element connected to the gas supply line, wherein the gas supply line is configured to be extended from a stored position to an extended position by rotating the rotary element.

11. The bleeding control device according to claim 1, wherein the gas supply line comprises a first part and a second part, wherein the second part is movable within an inner volume of the first part.

12. The bleeding control device according to claim 11, wherein the first part includes a first port and the second part includes a second port, wherein the inflation means is fluidly connected to the inflatable balloon through the first port, the inner volume and the second port.

13. The bleeding control device according to claim 12, wherein the second part is configured to move in an extending direction upon the inner volume being pressurized with gas.

14. The bleeding control device according to claim 13, further comprising a spring arranged within the inner volume configured to assist moving the second part in the extending direction with a spring force.

15. The bleeding control device according to claim 14, further comprising a contact switch, wherein the contact switch is configured to cause, upon actuation, the inner volume to become pressurized with gas, thereby moving the second part in the extending direction with the assist of the spring force of the spring.

16. The bleeding control device according to claim 1, wherein the inflatable balloon comprises a tubing running along a length of the balloon and a one-way valve configured to allow gas to exit the tubing.

17. The bleeding control device according to claim 1, further comprising a removable sheath covering the inflatable balloon.

18. The bleeding control device according to claim 1, further comprising an external gas input connection fluidly connected to the inflatable balloon through the gas supply line.

19. The bleeding control device according to claim 18, wherein the external gas input connection comprises a Luer lock.

20. The bleeding control device according to claim 1, further comprising an air chamber and a regulator, wherein the inflation means is fluidly connected to the inflatable balloon through the air chamber and the regulator, and wherein the air chamber and regulator are configured to maintain the inflatable balloon at a predetermined pressure or at a selected pressure.

21. The bleeding control device according to claim 1, further comprising a contact switch, wherein the contact switch is configured to cause, upon actuation, at least a portion of the gas supply line to extend away from the housing.

22. The bleeding control device according to claim 1, wherein the transmitter is configured to transmit the location information encrypted and/or through spread spectrum.

23. The bleeding control device according to claim 1, wherein the bleeding control device is configured to transmit an initial message before transmitting the location information.

24. A bleeding control device comprising:

a housing;

an outer inflatable balloon arranged within and/or connected to the housing;

an inner inflatable balloon arranged within the outer inflatable balloon;

inflation means arranged within and/or connected to the housing;

a gas supply line arranged within and/or connected to the housing; and a transmitter configured to transmit location information of the bleeding control device only after receiving a valid signal from an authorized medic or response unit;

wherein the inflation means is fluidly connected to the inner inflatable balloon through the gas supply line.

* * * * *